(12) United States Patent
Goncalves Da Costa (10) Patent No.: US 9,789,217 B2
(45) Date of Patent: Oct. 17, 2017

(54) PACKAGING AND TRANSPORTATION KIT FOR HYDROGEN PEROXIDE OR OTHER CHEMICAL PRODUCT USED IN STERILIZATION OR DISINFECTION EQUIPMENTS AND RESPECTIVE SUPPLYING SYSTEM

(71) Applicant: Helder Goncalves Da Costa, Boticas (PT)

(72) Inventor: Helder Goncalves Da Costa, Boticas (PT)

( * ) Notice: Subject to any disclaimer, the term of this patent is extended or adjusted under 35 U.S.C. 154(b) by 0 days.

(21) Appl. No.: 14/888,158

(22) PCT Filed: Apr. 30, 2013

(86) PCT No.: PCT/PT2013/000025
§ 371 (c)(1),
(2) Date: Oct. 30, 2015

(87) PCT Pub. No.: WO2014/178740
PCT Pub. Date: Nov. 6, 2014

(65) Prior Publication Data
US 2016/0058902 A1   Mar. 3, 2016

(51) Int. Cl.
*A61L 2/26* (2006.01)
*B65D 81/26* (2006.01)
(Continued)

(52) U.S. Cl.
CPC ............... *A61L 2/26* (2013.01); *A61L 2/186* (2013.01); *B65D 25/08* (2013.01); *B65D 77/04* (2013.01);
(Continued)

(58) Field of Classification Search
CPC .......................................... A61L 2/26
(Continued)

(56) References Cited

U.S. PATENT DOCUMENTS 5,199,795 A    4/1993 Russo et al.
5,863,496 A *  1/1999 McElhany ............... A61L 2/08
                                          383/113

(Continued)

FOREIGN PATENT DOCUMENTS

EP    0341056     5/1989
FR    2668755 A1  5/1992
(Continued)

*Primary Examiner* — Christine T Mui
(74) *Attorney, Agent, or Firm* — Porzio Bromberg Newman (57) ABSTRACT

The present invention refers to a Packaging and transportation kit for hydrogen peroxide or other chemical products used as sterilizing or disinfecting agents in sterilization or disinfection equipment that prevents leakage of the product. It also refers to the respective supplying system.

The referred packaging and transportation kit comprises a primary recipient or a set of primary recipients (1, 12) made of material that is compatible with the chemical product used; a sealing membrane or nano-membrane (2.1); a separation membrane or nano-membrane (2.2) of the primary recipient (1, 12) that divides it into different parts; with or without a capsule (3) with one or more holes; a super absorbent material (4.1) applied around the recipient(s) (1); an absorbent material (4.2) that can be inserted in the interior of the recipient (1) together with the liquid; a chip/RFID with memory and/or color code system, and/or a barcode system, and/or a QR code system; a temperature and/or humidity indicator (6, 6.1); a leakage indicator (7); and an external packing of resistant material (8).

15 Claims, 6 Drawing Sheets

(51) Int. Cl.
  *B65D 77/04* (2006.01)
  *B65D 85/84* (2006.01)
  *B65D 25/08* (2006.01)
  *B65D 79/02* (2006.01)
  *A61L 2/18* (2006.01)
  *F17C 13/02* (2006.01)

(52) U.S. Cl.
  CPC .......... *B65D 77/0426* (2013.01); *B65D 79/02* (2013.01); *B65D 81/264* (2013.01); *B65D 85/84* (2013.01); *F17C 13/02* (2013.01); *B65D 2203/10* (2013.01); *F17C 2227/0135* (2013.01)

(58) Field of Classification Search
  USPC .......... 422/401, 400, 50; 137/551, 240, 238; 206/204
  See application file for complete search history.

(56) References Cited

U.S. PATENT DOCUMENTS

| | | | | |
|---|---|---|---|---|
| 5,960,956 | A | * | 10/1999 | Langanki ................ A01N 1/02 206/364 |
| 7,300,637 | B2 | * | 11/2007 | Lin ........................... A61L 2/07 422/292 |
| 7,811,530 | B2 | * | 10/2010 | Morrison ................ A61L 2/186 422/28 |
| 2001/0050237 | A1 | | 12/2001 | Hacikyan |
| 2011/0076192 | A1 | | 3/2011 | Robitaille et al. |
| 2013/0095010 | A1 | | 4/2013 | Koyama |

FOREIGN PATENT DOCUMENTS

| WO | WO 98/46994 | * 10/1998 | ............. G01N 33/49 |
|---|---|---|---|
| WO | 2009008755 A1 | 1/2009 | |
| WO | 2010006355 A1 | 1/2010 | |

* cited by examiner

PACKAGING AND TRANSPORTATION KIT FOR HYDROGEN PEROXIDE OR OTHER CHEMICAL PRODUCT USED IN STERILIZATION OR DISINFECTION EQUIPMENTS AND RESPECTIVE SUPPLYING SYSTEM

The present invention refers to a packaging and transportation kit for hydrogen peroxide or other chemical product used as sterilizing or disinfecting agent (such as peracetic acid, formaldehyde, polypropylene oxide and alcohols), in sterilization or disinfection equipment that prevents leakage of the product, and refers also to the respective supplying system.

STATE OF THE ART

Document WO 2010/006355 refers to a bottle with sealing membrane permeable for gases and impermeable for liquids.

Document FR 2668755 describes a protection receptacle with an absorbent filling for bottles or other recipients containing dangerous products.

Document EP 0341056 refers to a receptacle with an absorbent material.

Also to be referred is patent application PCT n. 2011000047 in name of the applicant, which describes a packaging and transportation kit of chemical products used as sterilizing agents.

Advantages of the Invention

The present invention has the advantages of including:

A recipient or a set of recipients on a base capable of transporting hydrogen peroxide or other chemical products used as sterilizing or disinfecting agents (such as peracetic acid, formaldehyde, polypropylene oxide and alcohols) in sterilizers of medical devices or industrial sterilizers, or mechanical disinfection systems, or ambient disinfection systems, without product leakage to the exterior of the packing.

Primary recipient and/or external packing with recognizing system through RFID and/or color code system and/or barcode system and/or QR code system, capable to inform about expiration date, batch number of the product and/or other information, in order to make the product exclusive for a machine ensuring the reproducibility of the sterilization or disinfection cycles by being recognized exclusively by a determined equipment.

Primary recipient capable to resist a pressure relation of up to 400 N (newton) for 150 ml, with the ability to allow the gas exit from the interior without liquid leakage.

Primary recipient that can be rigid or flexible, with a sealing membrane or nano-membrane. In case of rigid recipients the sealing membrane is applied on the whole surface of the opening of the recipient, this recipient may be of "yogurt cup" type, where the surface of the opening is bigger than the bottom of the recipient itself. In case of flexible recipients, such as "saline bag" type, the membrane is applied on the liquid withdrawal zone.

Primary recipient that, being rigid or flexible, can be divided into parts by a separation membrane. In this case in one side the chemical product will be inserted in liquid state and in the other side will be inserted an absorbent material to absorb the liquid in case of lateral impact that leads to rupture of the separation membrane. This recipient separated by a membrane can also be used for packaging and transportation of hydrogen peroxide in solid state in one side of the membrane and the necessary liquid for dilution of it in the other side of the membrane.

Automatic supplying system that prevents the operator to get in contact with the sterilizing or disinfecting chemical product.

DESCRIPTION OF THE DRAWINGS

The signals of reference indicated in the figure are explained below.

1—Primary recipient made of material compatible with the chemical product;
2.1—Sealing membrane or nano-membrane of PTFE or other compatible material sealed on the whole surface of the opening of the primary recipient (1);
3—Capsule that can be threaded or not;
4.1—Super-absorbent material, of PE or other materials compatible with the chemical product;
4.2—Absorbent material of PE or other materials compatible with the chemical product that can be inserted inside the primary recipient (1) containing the chemical product;
5—Chip/RFID and/or color code, and/or barcode, and/or QR code;
6—Temperature indicator;
7—Leakage indicator;
8—External packing.

The signals of reference indicated in the figure are explained below.

1—Primary recipient made of material compatible with the chemical product;
2.1—Sealing membrane or nano-membrane, made of PTFE or other compatible material, sealed on the whole surface of the opening of the primary recipient (1);
2.2—Separation membrane or nano-membrane made of PTFE or other compatible material, sealed to the walls of the recipient (1) dividing it into more than one part in any angle of the recipient (1);
3—Capsule that can be threaded or not;
4.1—Super absorbent material made of PE or other materials compatible with the chemical product;
4.2—Absorbent material made of PE or other materials compatible with the chemical product that can be inserted in one of the sides of the primary recipient (1) containing the chemical product;
4.3—Dry absorbent material made of PE or other material compatible with the chemical product that can be inserted in the other side of the primary recipient (1);
5—Chip/RFID and/or color code, and/or barcode, and/or QR code;
6—Temperature indicator;
7—Leakage indicator;
8—External packing.

The signals of reference indicated in the figure are explained below:
1—Primary recipient made of material compatible with the chemical product;
2.1—Sealing membrane or nano-membrane made of PTFE or other compatible material, sealed on the whole surface of the opening of the primary recipient (1);
2.2—Separation membrane or nano-membrane made of PTFE or other compatible material, sealed on the walls of the recipient (1) dividing it into more than one part in any angle of the recipient (1);
3—Capsule that can be threaded or not;
4.1—Super absorbent material made of PE or other materials compatible with the chemical product;
5—Chip/RFID and/or color code, and/or barcode, and/or QR code;
6—Temperature indicator;
7—Leakage indicator;
8—External packing;
9—Liquid for dilution of the chemical product;
10—Chemical product in solid state;
11—Rupture device for the separation membrane (2.2).

The signals of reference indicated in the figure are explained below:
12—Flexible primary recipient made of material compatible with the chemical product;
13—Sealing membrane or nano-membrane made of PTFE or other compatible material, sealed on the liquid withdrawal zone;
2.2—Separation membrane or nano-membrane made of PTFE or other compatible material sealed on the walls of the recipient (12) dividing it into more than one part in any angle of the recipient (12);
14—Liquid withdrawal zone;
4.1—Super absorbent material made of PE or other material compatible with the chemical product;
4.2—Absorbent material made of PE or other material compatible with the chemical product that can be inserted in one side of the primary recipient (12) containing the chemical product;
4.3—Dry absorbent material made of PE or other material compatible with the chemical product that can be inserted in the other part of the primary recipient (12);
5—Chip/RFID and/or color code, and/or barcode, and/or QR code;
6—Temperature indicator;
7—Leakage indicator;
8—External packing;
15—Compression device of the flexible primary recipient (12).

The signals of reference indicated in the figure are explained below:
16—Hydrogen peroxide or other chemical product used, in solid state;
17—Protection membrane or nano-membrane;
1—Primary recipient made of material compatible with the chemical product;
4—Super absorbent material made of PE or other materials compatible with the chemical product;
5—Chip/RFID and/or color code, and/or barcode, and/or QR code;
6.1—Temperature and/or humidity indicator;
8—External packing.

With the configurations presented in FIGS. 2 to 5 the packaging and transportation kit for hydrogen peroxide or other chemical products allows several options for the transportation of the chemical product by having inside the primary recipient (1, 12) a separation membrane or nano-membrane (2.2) made of PTFE or other material compatible with hydrogen peroxide or other chemical products used, sealed to the walls of the recipient (1).

It is thus possible that the primary recipient (1, 12) may contain in one side the chemical product in liquid state and the other side empty so that in the event of an impact on the side of the recipient (1) where the liquid is, there may occur one of the two following situations: Either does the separation membrane (2.2) absorb the impact moving into the empty space or, in case of rupture of this membrane, the liquid occupies the free space of the recipient (1).

The recipient (1) can contain on one side of the membrane (2.2) the chemical product in liquid state and on the other side of the membrane (2.2) an absorbent material (4.2) that will absorb the liquid and retain it in the interior of the recipient (1) in case of rupture of the separation membrane (2.2), or it is also possible that the recipient (1) contains on one side the chemical product in liquid state in an absorbent material (4.2) and on the other side of the separation membrane (2.2) a dry absorbent material (4.3) to absorb the chemical product in case of accidental compression of the recipient (1) on the side where the absorbent (4.2) containing the liquid is.

There are more possible combinations of products on the different sides of the separation membrane (2.2) of the primary recipient (1).

The signals of reference indicated in the figure are explained below:
18—Connection between perforation needle and peristaltic pump of refilling;
1—Primary recipient of the sterilizing or disinfecting agent;
5—Chip/RFID and/or color code, and/or barcode, and/or QR code;
19—Drawer of supplying system.

20—Reader/writer of RFID, or color code, or barcode, or QR code;
21—Control board of servo motor of the perforation needle;
22—Control board of servo motor of drawer of supplying system;
23—Servo motor of perforation needle;
24—Servo motor of supplying system drawer;
25—Limit switch of supplying system drawer;
26—Limit switch of the perforation needle;
27—Perforation needle;
28—Compression device and liquid sensor.

DETAILED DESCRIPTION OF THE INVENTION

The invention will now be described as a non-limitative example with reference to the attached drawings.

The present invention refers to a packaging and transportation kit for hydrogen peroxide or other chemical products (such as peracetic acid, formaldehyde, polypropylene oxide and alcohols) in sterilization or disinfection equipments, in liquid state or associated to a super absorbent product and/or nano technology, of PE or other materials compatible with the chemical product used as sterilizing or disinfecting agent namely in sterilizers and/or mechanical disinfection systems or ambient disinfection systems that work with simple hydrogen peroxide or compound hydrogen peroxide, or with hydrogen peroxide PLASMA or with hydrogen peroxide to produce ozone ($O_3$) or with other chemical products, and that prevents possible leakage of the product to the exterior of the external packing.

The present invention also refers to an automatic supplying system of the sterilizing/disinfecting agent from the primary recipient.

Figure 1:
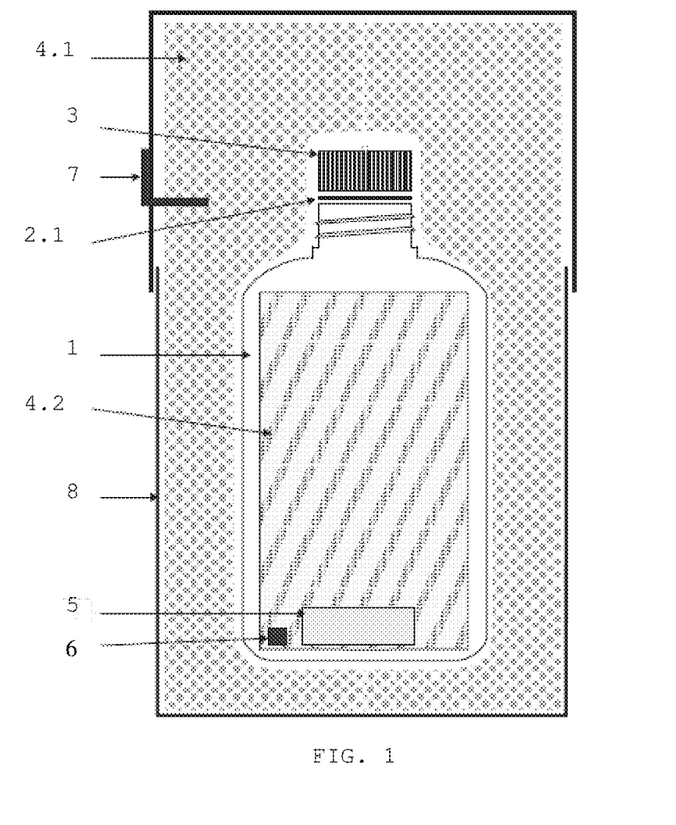
FIG. 1 illustrates a schematic drawing of the packaging and transportation kit for hydrogen peroxide or other chemical products with absorbent material inside the primary recipient.

Referring to FIG. 1, the packaging and transportation kit for hydrogen peroxide or other chemical products used as sterilizing or disinfecting agent with absorbent material inside the primary recipient is composed by:
- a primary recipient (1) of polyethylene (PE) or high density polyethylene (HDPE) or other material compatible with hydrogen peroxide or other chemical products used, that has a capacity from 2 milliliters to 60 liters;
- A sealing membrane or nano-membrane (2.1) of PTFE or other material compatible with hydrogen peroxide or other chemical products used, that is sealed on the whole surface of the opening of the primary recipient (1), with the ability to allow the gas exit of the recipient (1) and that allows that a recipient of PE (1) resists to a pressure relation of up to 400 N (newton) for 150 ml, without liquid leakage;
- A capsule that can be threaded or not (3) that can be applied or not, with one or more holes to allow the gas exit;
- A super absorbent material (4.1) that can be solid or gelatinous or fibrous or composed by nanotechnology, of PE or other material compatible with hydrogen peroxide or other chemical products used, applied around the primary recipient (1), covering it completely or partly, capable of retaining possible liquid leakage of the primary recipient (1);
- An absorbent material (4.2) that can be solid or gelatinous or fibrous or composed by nanotechnology, of PE or other material compatible with hydrogen peroxide or other chemical products used, that can be inserted inside the primary recipient (1) with the objective to retain the chemical product in its interior in case of damage of the primary recipient (1);
- A chip/RFID with memory and/or color code system, and/or a barcode system, and/or a QR code system (5) that allows the product to be dedicated to a specific equipment and recognized by it and that indicates the batch number, the production date, the expiration date, and/or other information;
- A chemical and/or electronic temperature indicator (6) that records the maximum temperature the kit was exposed to;
- A leakage indicator (7) composed by material sensitive to hydrogen peroxide or other chemical products used, that changes its color when in contact with the chemical product and that notifies externally the presence of leaked product on the inside;
- An external package of resistant material (8) compatible with hydrogen peroxide or other chemical products used.

Figure 2:
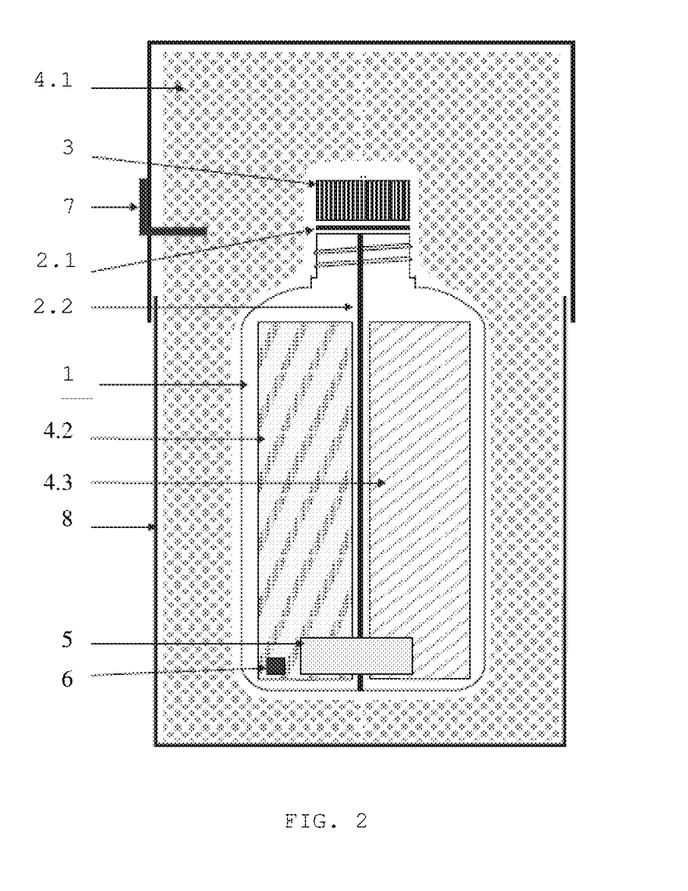
FIG. 2 illustrates a schematic drawing of the packaging and transportation kit for hydrogen peroxide or other chemical products, with a separation membrane that divides the primary recipient into two parts. One of these parts contains the chemical product in an absorbent material and the other part containing a dry absorbent material for absorption of liquid leakage in case there is a rupture of the separation membrane caused by strong lateral impact.

Referring to FIG. 2 the packaging and transportation kit for hydrogen peroxide or other chemical products, with a separation membrane dividing the primary recipient into two parts, one of them containing the chemical product in an absorbent material and the other one containing a dry absorbent material for absorption of liquid leakage in case there is a rupture of the separation membrane caused by a strong lateral impact, is composed by:
- a primary recipient (1) made of polyethylene (PE) or high density polyethylene (HDPE) or other material compatible with hydrogen peroxide or other chemical products used, that has a capacity from 2 milliliters to 60 liters;
- a sealing membrane or nano-membrane (2.1) made of PTFE or other material compatible with hydrogen peroxide or other chemical products used, that is sealed on the whole surface of the opening of the primary recipient (1), that allows the exit of gas out of the recipient (1) and that allows that a recipient made of PE (1) resists to a pressure relation of up to 400 N for 150 ml without leakage of liquid;
- A separation membrane or nano-membrane (2.2) made of PTFE or other material compatible with hydrogen peroxide or other chemical products used, that is sealed to the walls of the recipient (1) dividing it into more than one part in any angle of the recipient (1), one of the parts containing the chemical product in absorbent material (4.2) and the other part containing a dry absorbent material (4.3) for absorption of leakage of liquid in case there is a rupture of the separation membrane (2.2) caused by strong lateral impact;
- A capsule that can be threaded or not (3) that can be applied or not and that has one or more holes that allow the gas exit;
- A super absorbent material (4.1) that can be solid or gelatinous or fibrous or composed by nanotechnology, of PE or other material compatible with hydrogen peroxide or other chemical products used, applied around the primary recipient (1), covering it completely or partly, capable to retain possible liquid leakage from the primary recipient;
- An absorbent material (4.2) that can be solid or gelatinous or fibrous or composed by nanotechnology, of PE or other material compatible with hydrogen peroxide or other chemical products used, that can be inserted in one of the sides of the primary recipient (1) containing the chemical product;

A dry absorbent material (4.3) that can be solid or gelatinous or fibrous or composed by nanotechnology, of PE or other material compatible with hydrogen peroxide or other chemical products used, that can be inserted in one side of the primary recipient (1) with the objective of absorbing the chemical products in case there is an accidental compression of the recipient (1) that causes a rupture of the separation membrane or nano-membrane (2.2);

A chip/RFID with memory and/or color code system and/or barcode system and/or QR code system (5) that allows the product to be dedicated to a specific equipment and recognized by it and that indicates batch number, production date, expiration date and/or other information;

A chemical and/or electronic temperature indicator (6) that records the maximum temperature the kit was exposed to;

A leakage indicator (7) composed by material that is sensitive to hydrogen peroxide or other chemical products used, that changes its color when getting in contact with the chemical product and that notifies externally the presence of leaked product on the inside;

An external package made of resistant material (8) compatible with hydrogen peroxide or other chemical products used.

Figure 3:
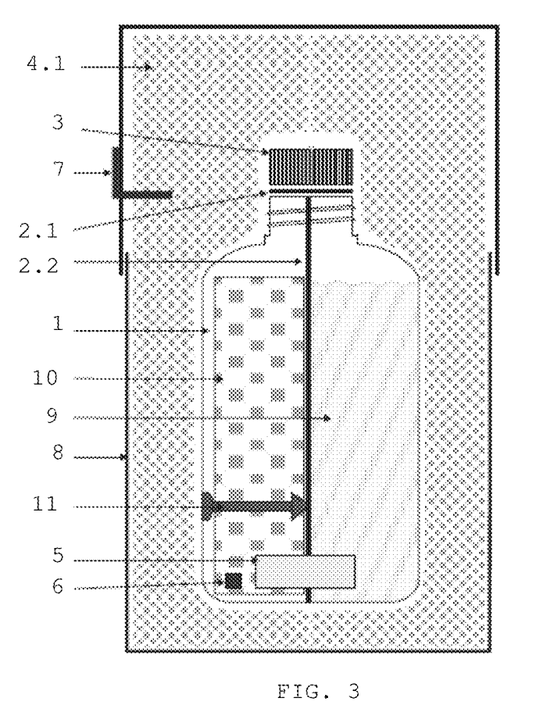
FIG. 3 illustrates a schematic drawing of the packaging and transportation kit for hydrogen peroxide or other chemical products with a separation membrane that divides the primary recipient into two parts. One of these parts containing the hydrogen peroxide in solid state and the other part containing the adequate liquid for the dilution of hydrogen peroxide by action of a rupture device of the separation membrane.

Referring to FIG. 3 the packaging and transportation kit for hydrogen peroxide or other chemical products, with a separation membrane dividing the primary recipient into two parts, one of it containing hydrogen peroxide in solid state and the other part containing the adequate liquid for dilution of the hydrogen peroxide by action of a device that ruptures the separation membrane, is composed by:

A primary recipient (1) made of polyethylene (PE) or high density polyethylene (HDPE) or other material compatible with hydrogen peroxide or other chemical product used, that has a capacity from 2 milliliter to 60 liters;

A sealing membrane or nano-membrane (2.1) made of PTFE or other material compatible with hydrogen peroxide or other chemical products used, that is sealed on the whole surface of the opening of the primary recipient (1), that allows the gas exit out of the recipient (1) and that allows that a recipient of PE (1) resists to a pressure relation of up to 400 N for 150 ml without liquid leakage;

A separation membrane or nano-membrane (2.2) of PTFE or other material compatible with hydrogen peroxide or other chemical products used, that is sealed to the walls of the recipient (1) dividing it into more than one part in any angle of the recipient (1), one of the parts containing the chemical product in solid state (10) and the other part containing an adequate liquid for dilution of the chemical product by action of a device (11) that ruptures the separation membrane (2.2);

A capsule that can be threaded or not (3) that can be applied or not, and that has one or more holes that allows the gas exit;

A super absorbent material (4.1) that can be solid or gelatinous or fibrous or composed by nanotechnology, of PE or other material compatible with hydrogen peroxide or other chemical products used, applied around the primary recipient (1), covering it completely or partly, capable of retaining liquid leakage of the primary recipient (1);

A chip/RFID with memory and/or color code system and/or barcode system and/or QR code system (5) that allows the product to be dedicated to a specific equipment and recognized by it and that indicates batch number, production date, expiration date and/or other information;

A chemical and/or electronic temperature indicator (6) that records the maximum temperature the kit was exposed to;

A leakage indicator (7) composed by material that is sensitive to hydrogen peroxide or other chemical product used that changes its color when it gets in contact with the chemical product and that notifies externally the presence of leaked product in the interior;

An external package made of resistant material (8) compatible with hydrogen peroxide or other chemical products used;

The adequate liquid (9) for dilution of the chemical product by action of a device (11) for rupture of the separation membrane (2.2);

hydrogen peroxide or other chemical product in solid state, as tablets or granulate or other (10);

a device (11) for rupture of the separation membrane (2.2) that is actuated automatically or manually.

Figure 4:
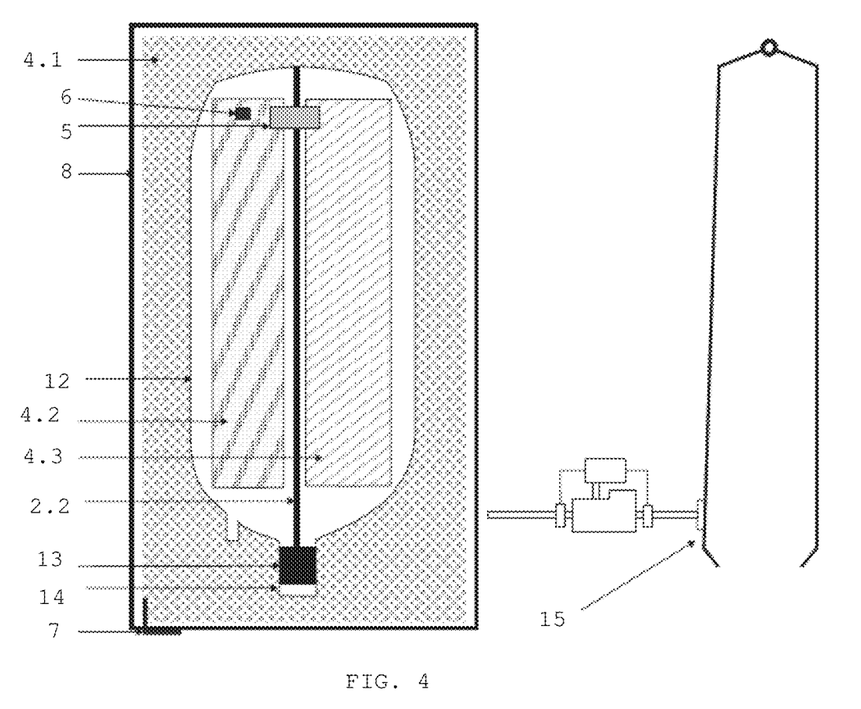
FIG. 4 illustrates a schematic drawing of the packaging and transportation kit for hydrogen peroxide or other chemical products where the primary recipient is flexible like a saline bag with a separation membrane dividing it into two parts. One of the parts containing the chemical product in an absorbent material and the other part containing a dry absorbent material for the absorption of liquid leakage in case there is a rupture of the separation membrane caused by a strong impact. Also includes the scheme of a compression device to compress the flexible primary recipient.

Referring to FIG. 4 the packaging and transportation kit for hydrogen peroxide or other chemical products, whose primary recipient is flexible, like a saline bag, with a separation membrane dividing it into two parts, one of these parts containing the chemical product in absorbent material and the other part containing dry absorbent material for absorption of liquid leakage in case there is a rupture of the separation membrane caused by strong impact, is composed by:

a primary flexible recipient (12) made of polyethylene (PE) or other material compatible with hydrogen peroxide or other chemical products used, with a capacity from 2 milliliters to 60 liters;

a sealing membrane or nano-membrane (13), made of PTFE or other material compatible with hydrogen peroxide or other chemical products used, sealed on the withdrawal area of the chemical product, that allows the exit of gas out of the recipient (12) without liquid leakage;

a separation membrane or nano-membrane (2.2) made of PTFE or other material compatible with hydrogen peroxide or other chemical product used, that is sealed to the walls of the recipient (12) dividing it into more than one part in any angle of the recipient (12), one of the parts containing the chemical product in absorbent material (4.2) and the other part containing dry absorbent material (4.3) for absorption of liquid leakage in case there is a rupture of the separation membrane (2.2) caused by strong lateral impact;

an area for withdrawal of the liquid chemical product (14);

a super absorbent material (4.1) that can be solid or gelatinous or fibrous or composed by nanotechnology, of PE or other material compatible with hydrogen or other chemical products used, applied around the primary recipient (12), covering it completely or partly, capable of retaining possible liquid leakage of the primary recipient (12);

an absorbent material (4.2) that can be solid or gelatinous or fibrous or composed by nanotechnology, of PE or other material compatible with hydrogen peroxide or other chemical products used, that can be inserted in one of the sides of the primary recipient (12) containing the chemical product;

a dry absorbent material (4.3), that can be solid or gelatinous or fibrous or composed by nanotechnology, of PE or other material compatible with hydrogen peroxide or other chemical products used, that can be inserted in the other side of the primary recipient (12) with the objective of absorbing the chemical product in case of an accidental compression of the recipient (12) that causes a rupture of the separation membrane or nano membrane (2.2);

A chip/RFID with memory and/or color code system and/or barcode system and/or QR code system (5) that allows the product to be dedicated to a specific equipment and recognized by it and that indicates batch number, production date, expiration date and/or other information;

A chemical and/or electronic temperature indicator (6) that records the maximum temperature the kit was exposed to;

A leakage indicator (7) composed by material that is sensitive to hydrogen peroxide or other chemical product used that changes its color when it gets in contact with the chemical product and that notifies externally the presence of leaked product in the interior;

An external package made of resistant material (8) compatible with hydrogen peroxide or other chemical products used;

A compression device (15) for the primary flexible recipient that is controlled by the automation system and that, after perforation of the sealing membrane (2.1) compresses the recipient (12) with the absorbent material (4.2) containing the chemical product in liquid state so that it can be removed by the needle.

Figure 5:
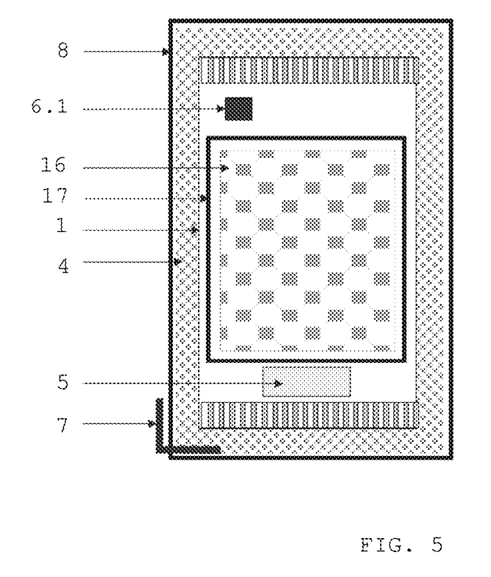
FIG. 5 illustrates a schematic drawing of the packaging and transportation kit for hydrogen peroxide or other chemical products in solid state, protected by absorbent material.
Figure 6:
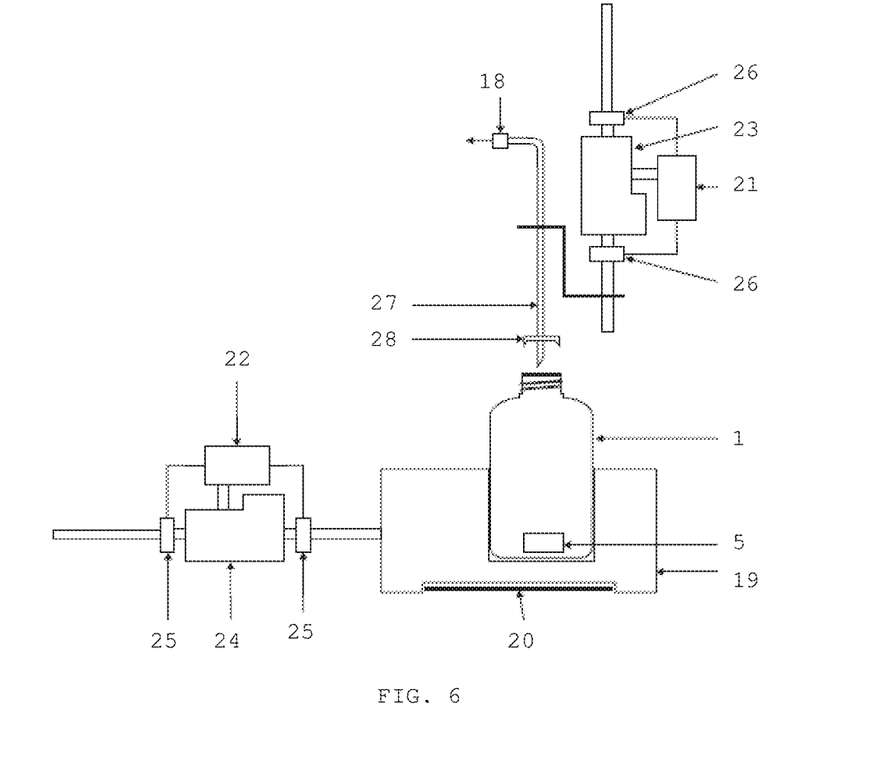
FIG. 6 illustrates a scheme of the automatic supplying system of the sterilizing or disinfecting agent from the primary recipient to the sterilization/disinfection equipment. In this system, after the withdrawal of the liquid of the primary recipient, a sensor on the perforation needle informs the automation system that the operator of the equipment can remove the primary recipient from the holder and close the drawer of the supplying system.

Referring to FIG. 5 the packaging and transportation kit for hydrogen peroxide or other chemical products in solid state, protected by absorbent material, is composed by:

hydrogen peroxide or other chemical product used, in solid state, as tablets, granulate or other (16);

a protection membrane or nano-membrane (17) that involves the hydrogen peroxide in solid state (16) that can be applied or not, made of PTFE or other material compatible with the chemical product used;

primary recipient (1) made of material compatible with hydrogen peroxide or other chemical products used;

a super absorbent material (4.1), that can be solid or gelatinous or fibrous or composed by nanotechnology, of PE or other material compatible with hydrogen peroxide or other chemical products used, applied around the primary recipient (1), covering it completely to prevent possible contact of the chemical product in solid state (16) with any liquid;

chip/RFID with memory and/or color code system and/or barcode system and/or QR code system (5) that allows the product to be dedicated to a specific equipment and recognized by it and that indicates batch number, production date, expiration date and/or other information;

a chemical and/or electronic temperature and/or humidity indicator (6.1) that records the maximum temperature and/or humidity the kit was exposed to;

an external package made of resistant material (8) compatible with hydrogen peroxide or other chemical products used;

Referring to FIG. 6 the automatic supplying system of the sterilizing or disinfecting agent from the primary recipient to the sterilization/disinfection equipment is composed by:

a mechanical connection (18) to connect the perforation needle (27) to the supply peristaltic pump of the sterilization or disinfection equipment;

a drawer of the supplying system (19) with a holder for the primary recipient (1) of hydrogen peroxide or other chemical product used;

a reader/writer of RFID or color code system or barcode system or QR code system (20) for recognition of the primary recipient (1);

a control board (21) of the servo motor of the perforation needle;

a control board (22) of the servo motor of the drawer of the supplying system;

a servo motor (23) of the perforation needle;

a servo motor (24) of the drawer of the supplying system;

a limit switch (25) of the drawer of the supplying system;

a limit switch (26) of the perforation needle;

a perforation needle (27) that perforates the sealing membrane or nano membrane (2.1) of the primary recipient (1) and removes the sterilizing or disinfecting agent;

a compression device and liquid sensor (28) that enters together with the perforation needle (27) in the primary recipient (1) and compresses the absorbent material (4.2) containing the chemical product in liquid state so that it can be removed through the needle (27).

The invention claimed is:

1. A packaging and transportation system for hydrogen peroxide or other chemical products in liquid form used as sterilizing or disinfecting agents in sterilization or disinfection equipment comprising a primary recipient made of polyethylene (PE) or high density polyethylene (HDPE) or other material compatible with the chemical product used; a sealing membrane or nano-membrane made of PTFE or other compatible material, sealed on the whole surface of an opening of the primary recipient, or on an area of liquid withdrawal that allows the exit of gas out of the primary recipient and that allows that the primary recipient made of PE resists to a pressure relation of up to 400 N for 150 ml without liquid leakage; a separation membrane or nano-membrane made of PTFE or other material compatible with hydrogen peroxide or other chemical product of liquid form used, that is sealed to the walls of the primary recipient dividing it into more than one part in any angle of the recipient; a capsule that can be threaded or not with one or more holes; a first absorbent material applied around the primary recipient covering it completely or partly capable of retaining possible liquid leakage from the primary recipient; a second absorbent material, placed inside the primary recipient adapted to retain the chemical product in an interior of the primary recipient in case of damage of the primary recipient; a chip/RFID with memory and/or color code system, and/or barcode system, and/or QR code system; a chemical and/or electronic temperature and/or humidity indicator; a leakage indicator and an external package of resistant material compatible with hydrogen peroxide or other chemical products used; and a holder placed in a supplying system of the sterilization or disinfection equipment, the primary recipient docks at the sterilization or disinfection equipment by the holder.

2. The packaging and transportation system for hydrogen peroxide or other chemical products, according to claim 1, wherein the primary recipient has a capacity from 2 milliliters to 60 liters.

3. The packaging and transportation system for hydrogen peroxide or other chemical products, according to claim 1, wherein the separation membrane or nano-membrane of the primary recipient, of PTFE or other material compatible with hydrogen peroxide or other chemical product used, sealed to the walls of the primary recipient and dividing it into more than one part in any angle of the primary recipient making possible that in one side of the separation membrane there is the chemical product in liquid state or in an absorbent material and in the other side of the separation membrane there is empty space or an absorbent material, or other possible combinations of these options.

4. The packaging and transportation system for hydrogen peroxide or other chemical products, according to claim 1, wherein the chip/RFID with memory and/or a color code system, and/or a barcode system and/or a QR code system, or a chemical or electronic temperature indicator, or other, applied on the primary recipient or on the external package or located inside the liquid, allows that the product can be recognized by a specific equipment to which it is dedicated and indicating the batch number, production date, expiration date, and/or other information of the product.

5. The packaging and transportation system for hydrogen peroxide or other chemical products, according to claim 1, wherein the chip/RFID with memory and/or a color code system, and/or a barcode system and/or a QR code system, can be applied on an exterior of the primary recipient, inside the primary recipient together with the liquid or on the external packaging.

6. The packaging and transportation system for hydrogen peroxide or other chemical products, according to claim 1, having a solid, gelatinous, fibrous or composed by nanotechnology, of PE or other material compatible with hydrogen peroxide or other chemical products used, the first absorbent material, applied around the primary recipient, covering it completely or partly retaining possible liquid leakage of the primary recipient, and absorbing impacts preventing damages on the primary recipient.

7. The packaging and transportation system for hydrogen peroxide or other chemical products, according to claim 1, wherein the absorbent material is made of PE or other material compatible with hydrogen peroxide or other chemical products inside the primary recipient that retains the chemical product in its interior in case of damages on the primary recipient.

8. The packaging and transportation system for hydrogen peroxide or other chemical products, according to claim 1, wherein the first and second absorbent materials comprise solid, gelatinous, fibrous or composed by nanotechnology of PE or other material compatible with hydrogen peroxide or other chemical products used, being used together, separately or in different combinations.

9. The packaging and transportation system for hydrogen peroxide or other chemical products, according to claim 1, wherein the external package is resistant and formed of corrugated plastic or other material compatible with hydrogen peroxide or other chemical products used.

10. The packaging and transportation system for hydrogen peroxide or other chemical products, according to claim 1, wherein the first and second absorbent materials comprise solid, gelatinous, fibrous or composed by nanotechnology of PE or other material compatible with hydrogen peroxide or other chemical products used, and being applied around the primary recipient containing the hydrogen peroxide or other chemical product in solid state preventing any contact of any liquid with the chemical product in solid state.

11. The packaging and transportation system for hydrogen peroxide or other chemical products, according to claim 1, further comprising a device for rupture of the separation membrane, actuated automatically or manually that provides contact between the hydrogen peroxide in solid state that is located in one side of the membrane with the adequate liquid for dilution of the chemical product that is located in the other side of the separation membrane.

12. The packaging and transportation system for hydrogen peroxide or other chemical products, according to claim 1, wherein the chemical and/or electronic temperature and/or humidity indicator registers the maximum temperature and/or humidity the kit was exposed to.

13. The packaging and transportation system for hydrogen peroxide or other chemical products, according to claim 1, wherein the leakage indicator is composed by material which is sensitive to hydrogen peroxide or other chemical product used, the leakage indicator changes its color when entering in contact with the chemical product notifying externally the presence of leaked product in the interior.

14. An automatic, electric or other, supplying system of a sterilizing or disinfecting agent from a packaging and transportation kit for hydrogen peroxide or other chemical products in liquid form to sterilization or disinfection equipment, wherein the packaging and transportation kit for hydrogen peroxide or other chemical products in liquid form comprises a primary recipient made of polyethylene (PE) or high density polyethylene (HDPE) or other material compatible with the chemical product used; a sealing membrane or nano-membrane made of PTFE or other compatible material, sealed on the whole surface of an opening of the primary recipient, or on an area of liquid withdrawal that allows the exit of gas out of the primary recipient and that allows that the primary recipient made of PE resists to a pressure relation of up to 400 N for 150 ml without liquid leakage; a separation membrane or nano-membrane made of PTFE or other material compatible with hydrogen peroxide or other chemical product of liquid form used, that is sealed to the walls of the primary recipient dividing it into more than one part in any angle of the primary recipient; a capsule that can be threaded or not with one or more holes; a first absorbent material applied around the primary recipient covering it completely or partly capable of retaining possible liquid leakage from the primary recipient; a second absorbent material placed inside the primary recipient adapted to retain the chemical product in an interior of the primary recipient in case of damage of the primary recipient; a chip/RFID with memory and/or color code system, and/or barcode system, and/or QR code system; a chemical and/or electronic temperature and/or humidity indicator; a leakage indicator and an external package of resistant material compatible with hydrogen peroxide or other chemical products used, the supplying system of a sterilizing or disinfecting agent comprising a supplying drawer with automatic opening, with opening and closing sensors, that has a holder for the primary recipient and a moving needle the holder for the primary recipient having a recognition system with a reader for RFID and/or color code and/or barcode and/or QR code, that interacts with the automation system of the sterilization or disinfection equipment, and by the withdrawal of the liquid from the primary recipient being made by perforation of the sealing membrane or nano-membrane that is sealed on the opening of the primary recipient and by a compression device for compressing the second absorbent material located in the interior of the primary recipient containing the hydrogen peroxide or other chemical products in liquid form and pumping the hydrogen peroxide or other chemical products in liquid form to a tank with controlled temperature by a Peltier plate that is part of the sterilization or disinfection equipment.

15. The automatic, electric or other, supplying system, according to claim 14, wherein at the end of the removal of the liquid from the primary recipient, a sensor at the perforation needle informs the automation system that the operator of the equipment can remove the primary recipient from the holder and close the drawer of the supplying system.

* * * * *